United States Patent
Almulhim

(10) Patent No.: US 11,678,874 B1
(45) Date of Patent: Jun. 20, 2023

(54) DOUBLE "J" LAPAROSCOPIC FASCIAL CLOSURE DEVICE

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/974,480

(22) Filed: Oct. 26, 2022

(51) Int. Cl.
*A61B 17/04* (2006.01)
*A61B 17/00* (2006.01)
*A61B 17/34* (2006.01)

(52) U.S. Cl.
CPC ...... *A61B 17/0469* (2013.01); *A61B 17/0057* (2013.01); *A61B 17/0482* (2013.01); *A61B 17/3417* (2013.01); *A61B 17/3421* (2013.01); *A61B 2017/00637* (2013.01); *A61B 2017/00663* (2013.01)

(58) Field of Classification Search
CPC ............ A61B 17/0482; A61B 17/3417; A61B 17/3421; A61B 2017/00637
See application file for complete search history.

(56) References Cited

U.S. PATENT DOCUMENTS

| | | |
|---|---|---|
| 5,320,632 A | 6/1994 | Heldmuller |
| 5,364,408 A | 11/1994 | Gordon |
| 5,368,601 A | 11/1994 | Sauer et al. |
| 5,374,275 A | 12/1994 | Bradley et al. |
| 5,540,704 A * | 7/1996 | Gordon ............ A61B 17/06066 606/139 |
| 5,573,540 A * | 11/1996 | Yoon .................. A61B 17/0469 606/139 |
| 5,713,910 A | 2/1998 | Gordon |

(Continued)

FOREIGN PATENT DOCUMENTS

| | | |
|---|---|---|
| CA | 2477397 A1 | 9/2003 |
| EP | 3346927 B1 | 2/2020 |

(Continued)

OTHER PUBLICATIONS

"V-Loc Wound Closure Device", Covidien, printed from Internet Aug. 2022.

*Primary Examiner* — Phong Son H Dang
(74) *Attorney, Agent, or Firm* — Nath, Goldberg & Meyer; Richard C. Litman

(57) ABSTRACT

The double "J" laparoscopic fascial closure device has a fixed jaw and a movable jaw pivotally attached to the fixed jaw. An elongated hollow tube or cannula extends from the fixed jaw. The end of the elongated cannula distal from the jaws has two needles mounted thereon defining a double "J" configuration. A spring mechanism or cable guide is attached to the hollow tube, and a cable extends between the fixed jaw and the movable jaw. The other end of the cable extends through the elongated hollow tube, through the spacer arms, and back towards the needles at the ends of the needle mount arms. A suture thread is attached to both needles so that the thread bridges the gap between fascia on opposite sides of the laparoscopic port incision when the needles are draw back through the fascia towards the incision.

10 Claims, 4 Drawing Sheets

(56) References Cited

U.S. PATENT DOCUMENTS

| | | | | |
|---|---|---|---|---|
| 5,860,991 | A * | 1/1999 | Klein | A61B 17/0057 606/139 |
| 6,743,241 | B2 * | 6/2004 | Kerr | A61B 17/0057 606/139 |
| 6,911,034 | B2 * | 6/2005 | Nobles | A61B 17/0057 606/147 |
| 7,722,629 | B2 * | 5/2010 | Chambers | A61B 17/0057 606/144 |
| 7,824,419 | B2 * | 11/2010 | Boraiah | A61B 17/3421 606/139 |
| 8,920,442 | B2 * | 12/2014 | Sibbitt, Jr. | A61B 17/0057 606/139 |
| 9,668,727 | B2 | 6/2017 | Heneveld | |
| 9,675,342 | B2 * | 6/2017 | Prior | A61B 17/0482 |
| 11,234,690 | B2 * | 2/2022 | Kumar | A61B 17/06066 |
| 11,406,374 | B2 * | 8/2022 | Roslin | A61B 17/0057 |
| 2003/0171764 | A1 | 9/2003 | Debbas | |
| 2005/0149066 | A1 * | 7/2005 | Stafford | A61B 17/0469 606/144 |
| 2013/0030450 | A1 | 1/2013 | Dreyfuss et al. | |
| 2017/0105712 | A1 | 4/2017 | Patel et al. | |

FOREIGN PATENT DOCUMENTS

| | | |
|---|---|---|
| GB | 2440792 A | 2/2008 |
| WO | 2021152604 A1 | 8/2021 |

\* cited by examiner

DOUBLE "J" LAPAROSCOPIC FASCIAL CLOSURE DEVICE

BACKGROUND

1. Field

The disclosure of the present patent application relates to instruments for performing laparoscopic surgery, and particularly to a double "J" laparoscopic fascial closure device for closing the fascia on opposite sides of a laparoscopic port opening at the conclusion of a laparoscopic procedure.

2. Description of the Related Art

Laparoscopic surgery is a type of minimally invasive procedure that is often performed in abdominal and pelvic surgery. Laparoscopic surgery is performed using a very small incision, usually 0.5 mm to 1.5 mm, in the area of the umbilicus, through which a short tube called a trocar is inserted. The abdomen is insufflated with carbon dioxide gas to separate the abdominal wall from the organs in the abdominal cavity, and a camera mounted on a rod is inserted through the trocar with a fiber optic light so that the surgeon can view televised images of the cavity. Other surgical instruments may be inserted through the trocar or through other small incisions in the abdomen or pelvis. Laparoscopic surgery offers many benefits over open surgery, e.g., less pain, reduced risk of hemorrhage, reduced hospital stay since many patients can go home the same day as surgery, and faster recovery time.

Once the surgery is completed, any incisions over 10 mm in length should be closed. Sometimes closure of the laparoscopic trocar port may be difficult, particularly in obese individuals, where the fascia may become separated from the skin due to adipose tissue, or where there may be some shifting in position of the organs relative to the port incision. Thus, a double "J" laparoscopic fascial closure device solving the aforementioned problems is desired.

SUMMARY

The double "J" laparoscopic fascial closure device has a fixed jaw and a movable jaw pivotally attached to the fixed jaw. An elongated hollow tube or cannula extends from the fixed jaw. The end of the elongated cannula distal from the jaws has two needles mounted thereon, including two short spacer arms extending perpendicular to the cannula in opposite directions and needle mount arms perpendicular to the spacer arms extending back in the direction of the jaws, defining a double "J" configuration. A spring mechanism or cable guide is attached to the hollow tube, and a cable extends between the fixed jaw and the movable jaw. The other end of the cable extends through the elongated hollow tube, through the spacer arms, and back towards the needles at the ends of the needle mount arms. A suture thread is attached to both needles so that the thread bridges the gap between fascia on opposite sides of the laparoscopic port incision when the needles are draw back towards the incision.

In use, the device is turned 90° to insert the offset needles through the port incision. Each needle has a needle shield disposed over the needle to prevent needle sticks and protect the tissue. The cable is connected to the needle shield by another spring mechanism. When the movable jaw handle is pressed towards the fixed jaw handle, the needle shield is retracted or pivoted open to expose the needle with the suture thread passing through the needle. When the movable jaw handle is released, the needle shield closes over the needle, clamping the suture thread so the thread does not accidentally disengage from the needle as the device is manipulated to position the needles and draw them through the fascia and other tissue and through the skin. The device is again turned 90° to position the needles for penetrating the fascia and other tissues and skin on opposite sides of the port incision and through the skin, where the ends of the suture thread are drawn out, then turned back again for removal through the port incision.

Preferably, the two needles are spaced apart about 2 cm to allow the suture thread to approximate the fascia on opposite sides of the incision before tying the suture without damaging the tissue.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The double "J" laparoscopic fascial closure device has a fixed jaw and a movable jaw pivotally attached to the fixed jaw. An elongated hollow tube or cannula extends from the fixed jaw. The end of the elongated cannula distal from the jaws has two needles mounted thereon, including two short spacer arms extending perpendicular to the cannula in opposite directions and needle mount arms perpendicular to the spacer arms extending back in the direction of the jaws, defining a double "J" configuration. A spring mechanism or cable guide is attached to the hollow tube, and a cable extends between the fixed jaw and the movable jaw. The other end of the cable extends through the elongated hollow tube, through the spacer arms, and back towards the needles at the ends of the needle mount arms. A suture thread is attached to both needles so that the thread bridges the gap between fascia on opposite sides of the laparoscopic port incision when the needles are draw back towards the incision.

In use, the device is turned 90° to insert the offset needles through the port incision. Each needle has a needle shield disposed over the needle to prevent needle sticks and protect the tissue. The cable is connected to the needle shield by another spring mechanism. When the movable jaw handle is pressed towards the fixed jaw handle, the needle shield is retracted or pivoted open to expose the needle with the suture thread passing through the needle. When the movable jaw handle is released, the needle shield closes over the needle, clamping the suture thread so the thread does not accidentally disengage from the needle as the device is manipulated to position the needles and draw them through the fascia and other tissue and through the skin. The device is again turned 90° to position the needles for penetrating the fascia and other tissues and skin on opposite sides of the port incision and through the skin, where the ends of the suture thread are drawn out, then turned back again for removal through the port incision.

Preferably, the two needles are spaced apart about 2 cm to allow the suture thread to approximate the fascia on opposite sides of the incision before tying the suture without damaging the tissue.

Figure 1:
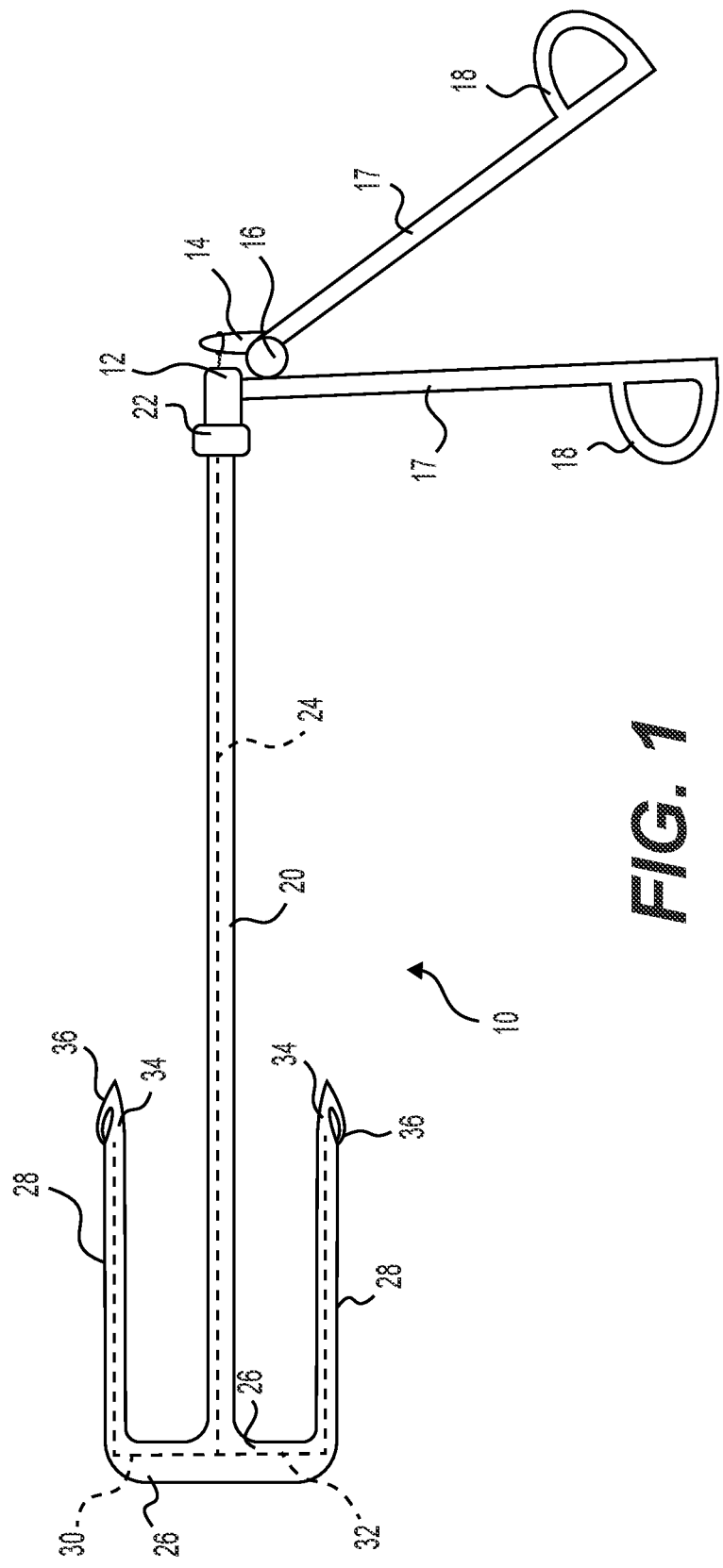
FIG. 1 is a front view of a double "J" laparoscopic fascial closure device.

As shown in FIG. 1, the double "J" laparoscopic fascial closure device 10 has a fixed jaw 12 and a movable jaw 14 pivotally attached to the fixed jaw 12 by a bolt or pivot pin 16. Each of the jaws 12, 14 has an elongate handle portion 17 terminating in a corresponding finger loop 18 or other gripping device, enabling the surgeon to pivot the movable jaw 14 rearward away from the fixed jaw 12. An elongated shaft, hollow tube or cannula 20 extends from the fixed jaw 12. A spring mechanism or cable guide 22 is attached to the hollow tube or cannula 20 adjacent the fixed jaw 12. A cable or other flexible member 24 extends between the movable jaw 14 and the fixed jaw 12, through the spring mechanism or cable guide 22, and through the hollow tube or cannula 20 so that when the jaw handles 17 are squeezed together, the movable jaw 14 is pulled rearward away from the fixed jaw 14, pulling the cable 24 rearward with it.

The end of the elongated cannula 20 distal from the jaws 12, 14 has two needles mounted thereon, the needle assembly including two short, hollow spacer or offset arms 26 extending perpendicular to the cannula 20 in opposite directions (superior and inferior) and two hollow needle mount arms 28 extending perpendicular to the spacer arms 26 back in the direction of the jaws 12, 14, defining a double "J" configuration. The cable 24 splits at the junction of the elongated tube or cannula 20 with the spacer arms 26, so that a superior branch cable 30 extends through the superior spacer arm 26 and corresponding needle mount arm 28, and an inferior branch cable 32 extends through the inferior spacer arm 26 and corresponding needle mount arm 28. In an alternative embodiment, the elongated hollow tube or cannula 20 is split or is a double cannula 20 to define two channels, and two cables extend from the jaws 12, 14 through the cannula 20, one cable branching through the superior spacer arm 26 and the other branching through the inferior spacer arm 26.

Each of the needle mount arms 28 has a suture needle 34 mounted thereon. Each of the suture needles 34 may have a needle shield 36 selectively covering the suture needle 34 to prevent accidental needle sticks when handling the instrument, and to selectively clamp opposing ends of a suture thread to the corresponding needles 34 when maneuvering the needles 34 within the abdominal or pelvic cavity. The superior branch cable 30 and the inferior branch cable 32 are connected either directly or through a spring mechanism to the corresponding needle shield 36. When the movable jaw 14 is pivoted rearward away from the fixed jaw 12, the system of cables 24, 30, 32 retracts the corresponding needle shields 36 to expose the suture needles 34. The spring mechanism or cable guide may include a locking mechanism to keep the needle shields 36 retracted while threading the suture needles 34 or while using the device 10 to draw the needles 34 and the suture thread through the skin and subcutaneous tissue.

Figure 2:
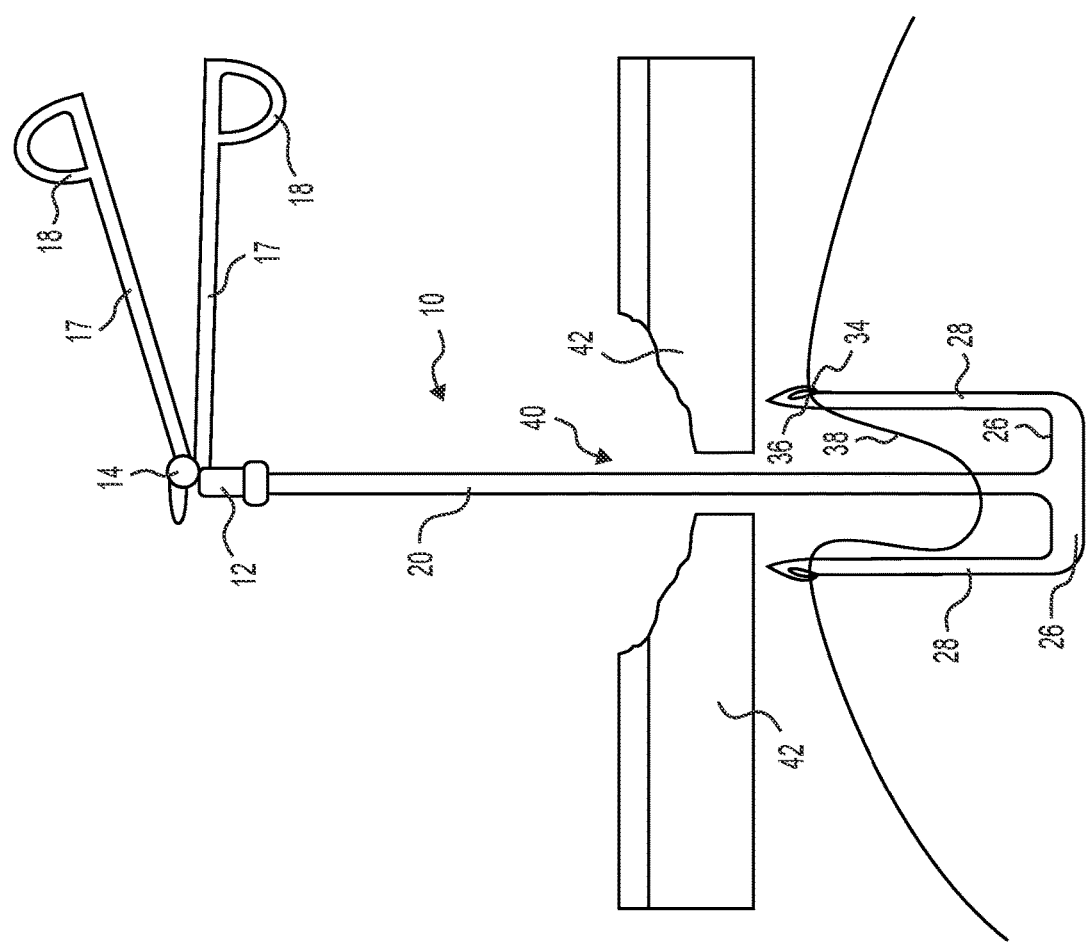
FIG. 2 is a schematic environmental front view of the double "J" laparoscopic fascial closure device of FIG. 1, shown inserted through the trocar port incision and aligned to pierce subcutaneous tissue on opposite sides of the incision.
Figure 3:
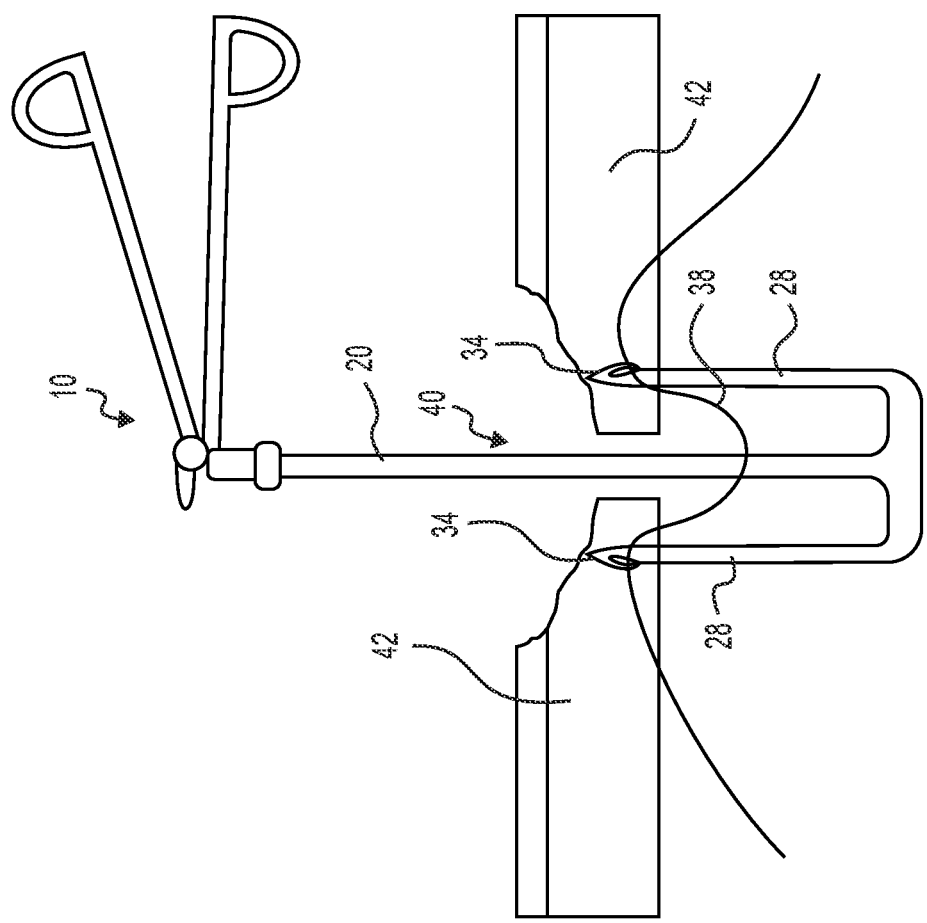
FIG. 3 is a schematic environmental front view of the double "J" laparoscopic fascial closure device of FIG. 1, shown inserted through the trocar port incision with both needles simultaneously piercing subcutaneous tissue on opposite sides of the incision.
Figure 4:
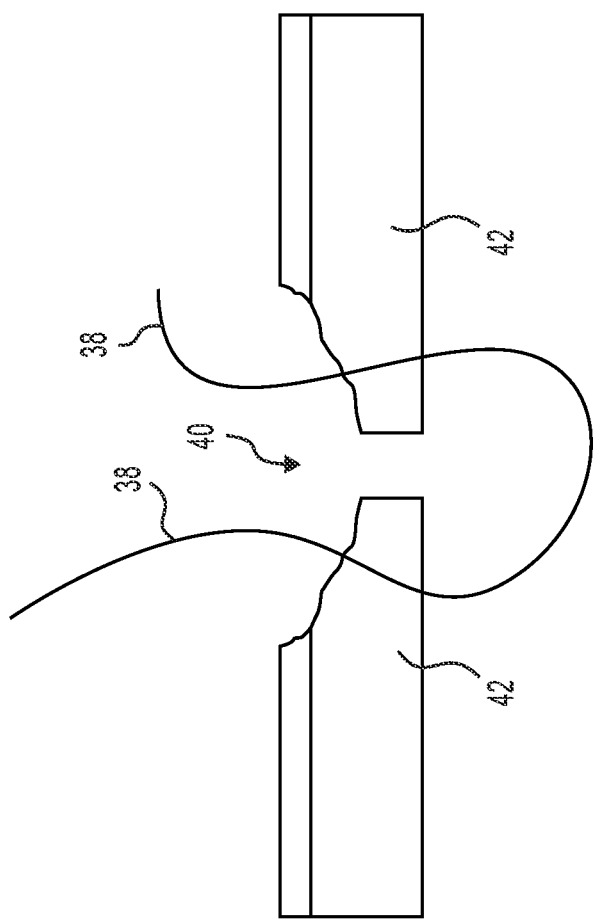
FIG. 4 is a schematic environmental view of the trocar port incision with the ends of the suture thread drawn out of opposite sides of the incision by the double "J" laparoscopic fascial closure device of FIG. 1 and ready to be tied.

As shown in FIG. 2, the device 10 is turned to place the spacer arms 26 parallel to the trocar port incision and insert the needle assembly into the abdominal or pelvic cavity, then turned 90° to position the needles 34 beneath the subcutaneous tissue 42 (including the fascia and layers of subcutaneous fat) on opposite sides of the trocar port incision with a suture thread 38 held by the needles 34 extending across the port opening 40. As shown in FIG. 3, the device 10 is pulled toward the abdominal wall so that both needles simultaneously pierce at least the fascia and layers of subcutaneous fat (and the skin when it is desired to close the fascia and skin by the same suture) until the ends of the suture thread 38 pass through the trocar port opening 40 and can be freed from the suture needles 34, as shown in FIG. 4. The fascia may then be drawn closed and a knot can be tied in the ends of the suture thread 38 to close the surgical wound.

For purposes of enablement and not by way of limitation, exemplary dimensions for the double "J" laparoscopic fascial closure device 10 include an elongated hollow tube or cannula having a length of 20 cm, a spacer arm 36 length of 1 cm each (a total of 2 cm between the needle mount arms 28), and a needle mount arm 28 length of 2 cm. These representative dimensions are sufficient to effect closure of the fascia in trocar port incisions up to 12 mm and 15 mm, even in obese and morbidly obese individuals. The double "J" laparoscopic fascial closure device 10 may be made from any rigid material suitable for laparoscopic surgical instruments, such as stainless steel or titanium alloys.

It is to be understood that the double "J" laparoscopic fascial closure device is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A double "J" laparoscopic fascial closure device, comprising:
 a fixed jaw having a handle extending therefrom;
 a movable jaw having a handle extending therefrom, the movable jaw being pivotally attached to the fixed jaw;
 an elongated shaft extending from the fixed jaw, the shaft having a distal end;
 a needle assembly mounted on the distal end of the elongated shaft, the needle assembly including:
  a pair of spacer arms rigidly extending perpendicularly from the distal end of the elongated shaft in opposite directions, respectively;
  a needle mount arm extending perpendicularly from each of the spacer arms, respectively, in a direction facing the jaws, the elongated shaft, the spacer arms, and
 the needle mount arms defining a double "J" configuration;
 a suture needle attached to each of the needle mount arms;
 wherein the needle mount arms are adapted for insertion through a trocar port incision into a patient's abdominal cavity with a suture thread extending between the two suture needles and alignment of the two suture needles below fascia on opposite sides of the trocar port incision so that the two suture needles may pierce the fascia and be drawn out of the abdominal cavity simultaneously on opposite sides of the trocar port incision, opposite ends of the suture thread being detached from the suture needles, drawn together and tied to close the fascia; wherein the elongated shaft comprises and elongated cannula; wherein said spacer arms and said needle mount arms are tubular; and a retractable needle shield disposed on each of the needle mount arms and covering each of the suture needles, respectively.

2. The double "J" laparoscopic fascial closure device according to claim 1, wherein the two suture needles are spaced apart by two centimeters.

3. The double "J" laparoscopic fascial closure device according to claim 1, further comprising a cable assembly attached to said movable jaw and extending through said fixed jaw, said cannula, said spacer arms, and said needle mount arms, the cable assembly being attached to said needle shields, whereby when said movable jaw is pivoted away from said fixed jaw, said needle shields are retracted to expose the suture needles.

4. The double "J" laparoscopic fascial closure device according to claim 3, further comprising a cable guide mounted on said cannula adjacent said fixed jaw, the cable assembly extending through the fixed jaw and the cable guide into said cannula.

5. The double "J" laparoscopic fascial closure device according to claim 1, wherein the double "J" laparoscopic fascial closure device is made from stainless steel.

6. A double "J" laparoscopic fascial closure device, comprising:
   a fixed jaw having a handle extending therefrom;
   a movable jaw having a handle extending therefrom, the movable jaw being pivotally attached to the fixed jaw;
   an elongated cannula extending from the fixed jaw, the cannula having a distal end;
   a needle assembly mounted on the distal end of the elongated shaft, the needle assembly including:
      a pair of tubular spacer arms rigidly extending perpendicularly from the distal end of the elongated cannula in opposite directions, respectively;
      a tubular needle mount arm extending perpendicularly from each of the spacer arms, respectively, in a direction facing the jaws, the elongated shaft, the spacer arms, and the needle mount arms defining a double "J" configuration;
      a suture needle attached to each of the needle mount arms;
   wherein the needle mount arms are adapted for insertion through a trocar port incision into a patient's abdominal cavity with a suture thread extending between the two suture needles and alignment of the two suture needles below fascia on opposite sides of the trocar port incision so that the two suture needles may pierce the fascia and be drawn out of the abdominal cavity simultaneously on opposite sides of the trocar port incision, opposite ends of the suture thread being detached from the suture needles, drawn together and tied to close the fascia; and a retractable needle shield disposed on each of the needle mount arms and covering each of the suture needles, respectively.

7. The double "J" laparoscopic fascial closure device according to claim 6, wherein the two suture needles are spaced apart by two centimeters.

8. The double "J" laparoscopic fascial closure device according to claim 6, further comprising a cable assembly attached to said movable jaw and extending through said fixed jaw, said cannula, said spacer arms, and said needle mount arms, the cable assembly being attached to said needle shields, whereby when said movable jaw is pivoted away from said fixed jaw, said needle shields are retracted to expose the suture needles.

9. The double "J" laparoscopic fascial closure device according to claim 8, further comprising a cable guide mounted on said cannula adjacent said fixed jaw, the cable assembly extending through the fixed jaw and the cable guide into said cannula.

10. The double "J" laparoscopic fascial closure device according to claim 6, wherein the double "J" laparoscopic fascial closure device is made from stainless steel.

* * * * *